United States Patent
Piorkowski et al.

(10) Patent No.: US 10,934,254 B2
(45) Date of Patent: Mar. 2, 2021

(54) USE OF AN ALCOHOL HYBRID TO MODIFY THE RHEOLOGY OF POLYETHOXYLATED ALCOHOL SULFATES

(71) Applicant: Henkel IP & Holding GmbH, Duesseldorf (DE)

(72) Inventors: Daniel Thomas Piorkowski, Fairfield, CT (US); David S. Stott, II, Madison, CT (US)

(73) Assignee: Henkel IP & Holding GmbH, Duesseldorf (DE)

( * ) Notice: Subject to any disclaimer, the term of this patent is extended or adjusted under 35 U.S.C. 154(b) by 48 days.

(21) Appl. No.: 15/831,518

(22) Filed: Dec. 5, 2017

(65) Prior Publication Data

US 2019/0169118 A1 Jun. 6, 2019

(51) Int. Cl.

| | |
|---|---|
| *C07C 305/10* | (2006.01) |
| *C08F 16/30* | (2006.01) |
| *C11D 3/34* | (2006.01) |
| *C11D 3/20* | (2006.01) |
| *C11D 1/722* | (2006.01) |
| *C11D 1/83* | (2006.01) |
| *C11D 3/37* | (2006.01) |
| *C11D 11/00* | (2006.01) |
| *C11D 1/29* | (2006.01) |

(52) U.S. Cl.
CPC ............ *C07C 305/10* (2013.01); *C08F 16/30* (2013.01); *C11D 1/29* (2013.01); *C11D 1/722* (2013.01); *C11D 1/83* (2013.01); *C11D 3/2003* (2013.01); *C11D 3/2006* (2013.01); *C11D 3/3409* (2013.01); *C11D 3/3707* (2013.01); *C11D 11/0094* (2013.01); *C11D 3/201* (2013.01); *C11D 3/2017* (2013.01); *C11D 3/2044* (2013.01); *C11D 3/2048* (2013.01); *C11D 3/2065* (2013.01)

(58) Field of Classification Search
CPC ....... C07C 305/10; C08F 16/30; C11D 1/722; C11D 3/2006; C11D 3/3409; C11D 3/2065
See application file for complete search history.

(56) References Cited

U.S. PATENT DOCUMENTS

| | | | |
|---|---|---|---|
| 4,092,273 A | * | 5/1978 | Inamorato ................ C11D 1/72 510/325 |
| 6,037,319 A | | 3/2000 | Dickler et al. |
| 7,259,134 B2 | | 8/2007 | Beckholt et al. |
| 2003/0114332 A1 | | 6/2003 | Ramcharan et al. |
| 2005/0101505 A1 | | 5/2005 | Wood |
| 2006/0094617 A1 | | 5/2006 | Price et al. |
| 2006/0166856 A1 | | 7/2006 | Petrat et al. |
| 2011/0112005 A1 | | 5/2011 | Brooker et al. |
| 2012/0135910 A1 | | 5/2012 | Gross et al. |
| 2014/0274859 A1 | | 9/2014 | Adamy |
| 2016/0177222 A1 | | 6/2016 | Bianchetti et al. |
| 2016/0376522 A1 | | 12/2016 | Bianchetti et al. |

FOREIGN PATENT DOCUMENTS

| | | |
|---|---|---|
| WO | 2004003120 A2 | 1/2004 |
| WO | 2006050298 A2 | 5/2006 |
| WO | 2016040629 A1 | 3/2016 |

OTHER PUBLICATIONS

DeGroot ("Sulphonation Technology in the Detergent Industry", 1991, 283 pages) (Year: 1991).*

* cited by examiner

*Primary Examiner* — Robert H Havlin
(74) *Attorney, Agent, or Firm* — Bojuan Deng

(57) ABSTRACT

In one embodiment, a polyethoxylated alcohol sulfate composition is provided which includes a polyethoxylated alcohol sulfate, such as sodium laureth ether sulfate (SLES), water, a mono-alcohol, and a polyol. The two alcohols form a synergistic blend, enabling a significant reduction of the viscosity of the polyethoxylated alcohol sulfate composition. Also provided is an embodiment of a method for modifying the rheology of polyethoxylated alcohol sulfate by use of a mono-alcohol and a polyol simultaneously. Finally provided is an embodiment of a detergent composition which is prepared by use of the polyethoxylated alcohol sulfate composition described herein, in addition to other commonly known ingredients.

13 Claims, 1 Drawing Sheet

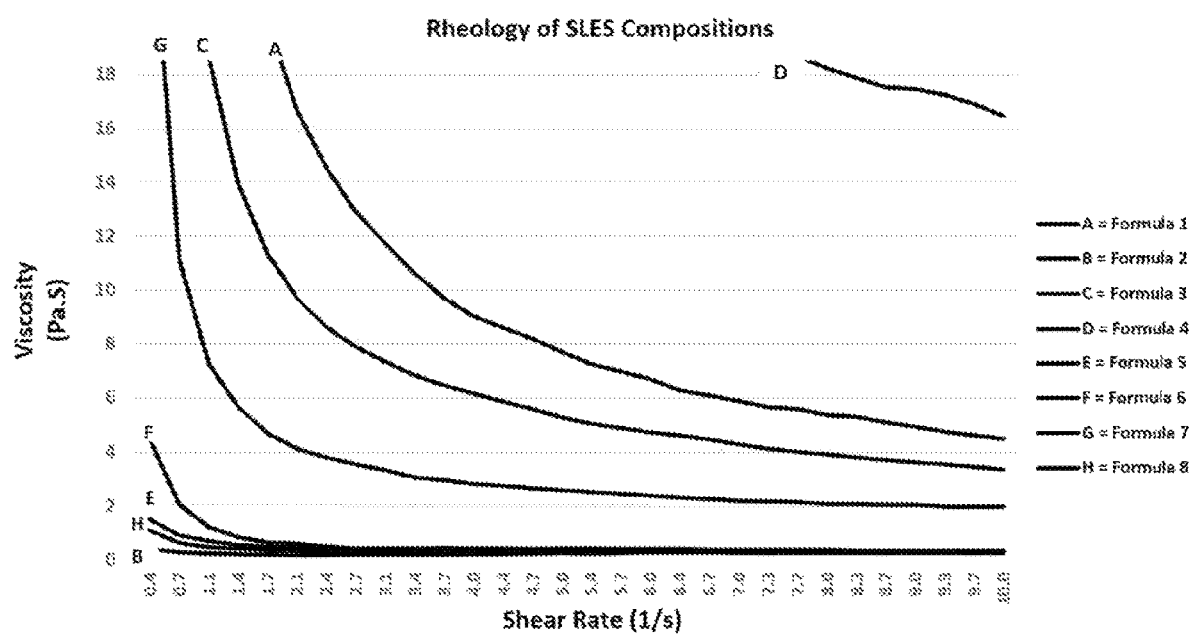

USE OF AN ALCOHOL HYBRID TO MODIFY THE RHEOLOGY OF POLYETHOXYLATED ALCOHOL SULFATES

FIELD OF THE INVENTION

The present invention relates to a method for modifying the rheology of a high viscous compound. In particular, the invention relates to a method for reducing viscosity of a polyethoxylated alcohol sulfate by adding an alcoholic hybrid as diluents. The present invention also relates to compositions comprising such diluents and a polyethoxylated alcohol sulfate.

BACKGROUND OF THE INVENTION

Sodium laureth ether sulfate (SLES), also known as sodium lauryl ether sulfate, is an anionic detergent and surfactant widely used in many laundry detergent products and personal care products. Its chemical formula is $CH_3(CH_2)_{11}(OCH_2CH_2)_nOSO_3Na$, wherein n may be 2 or 3. Commercial SLES typically has three ethoxyl groups (i.e., n=3) in the chemical formula.

SLES belongs to the genus of polyethoxylated alcohol sulfates, i.e., alkyl ether sulfates (AES) or alkyl polyethoxylate sulfates, having the following Formula (I):

$$R'\text{—}O\text{—}(C2H4O)n\text{-}SO3M' \qquad (I)$$

wherein R' is a C8-C20 alkyl group, n is from 1 to 20, and M' is a salt-forming cation, preferably, R' is C10-C18 alkyl, n is from 1 to 15, and M' is sodium, potassium, ammonium, alkylammonium, or alkanolammonium.

SLES is an inexpensive and effective at cleaning and emulsification. However, neat (i.e., 100%) SLES is difficult to use because it has a high viscosity. Moreover, SLES is a non-Newtonian fluid, meaning that its viscosity is variable based on applied stress or force, which makes it even more difficult to handle SLES.

As such, commercial SLES is supplied as a blend of SLES (60%), ethanol (12%), water (22%), alcohol ethoxylate 3EO (5%), and sodium sulfite (1%). The addition of ethanol and other solvents into SLES reduces the viscosity of the raw material and enables it to be easily flowable and processable at manufacturing plants.

However, ethanol has a low flash point (i.e., 16.60° C.) below average room temperature. According to the industry standards, for volatile solvents (e.g., ethanol), if the flash point is below a certain value (e.g., average room temperature), the raw material has to be shipped as a hazardous material and it also needs to be stored in a "bomb-proof" room just in case it flashes and causes an explosion. The inclusion of 12 parts ethanol makes the resulting SLES/ethanol blend a potential fire hazard during shipping, handling and batching with the SLES/ethanol blend, in particular on an industrial scale.

There is a need for an improved supply of SLES which not only has an improved rheology, but has a better fire safety profile. Preferably, the SLES supply contains less low flash point solvent, compared to the current commercial SLES raw material. More preferably, the SLES supply can be easily prepared either in situ (e.g., during a process of preparing laundry detergent or personal care products) or in advance (e.g., by preparing a stock supply of SLES).

BRIEF SUMMARY OF THE INVENTION

The inventors have unexpectedly found that a polyol and a mono-alcohol, when both were added into a polyethoxylated alcohol sulfate, such as sodium laureth ether sulfate (SLES), significantly reduces the viscosity of the polyethoxylated alcohol sulfate to a manageable level and enables it to be handled easily. Experimental data generated by the inventors show that a synergistic effect on the viscosity reduction has occurred by using the two different alcohols to modify the rheology of a polyethoxylated alcohol sulfate. Advantageously, the invention allows the reduction of the amount of a flammable alcohol needed to handle a polyethoxylated alcohol sulfate properly at manufacturing plants, which in turn, enables a safer material handling and final product batching.

In one aspect, the present invention provides a polyethoxylated alcohol sulfate composition which has an improved rheology. The term "an improved rheology" used herein refers to a reduced viscosity level of the polyethoxylated alcohol sulfate composition, as compared to the viscosity level of neat polyethoxylated alcohol sulfate. An improved rheology allows the polyethoxylated alcohol sulfate composition to be reasonably flowable and processable during manufacturing processes.

The polyethoxylated alcohol sulfate composition may consist essentially of a polyethoxylated alcohol sulfate having Formula (I), water, a mono-alcohol, and a polyol,

$$R'\text{—}O\text{—}(C2H4O)n\text{-}SO3M' \qquad (I)$$

wherein R' is a C8-C20 alkyl group, n is from 1 to 20, and M' is a salt-forming cation, preferably, R' is C10-C18 alkyl, n is from 1 to 15, and M' is sodium, potassium, ammonium, alkylammonium, or alkanolammonium.

According to some embodiments, the polyethoxylated alcohol sulfate is SLES in an amount ranging from about 20% to about 80%, from about 25% to about 75%, from about 30% to about 70%, from about 35% to about 65%, from about 40% to about 60%, from about 45% to about 55%, from about 40% to about 45%, or about 42%, by weight of the polyethoxylated alcohol sulfate composition. The polyethoxylated alcohol sulfate composition can thus be called SLES composition or SLES blend.

In some embodiments, water is in an amount ranging from about 5% to about 35%, from about 10% to about 30%, from about 15% to about 25%, from about 17% to about 22%, about 18%, about 19%, about 20%, or about 21%, by weight of the polyethoxylated alcohol sulfate composition.

According to some embodiments of SLES compositions, SLES may be provided as a premix of neat SLES and water, which can be called SLES premix. A preferred SLES premix consists of SLES and water in a ratio of 7:3 by weight.

It has been discovered that the addition of a polyol alone to an SLES premix does not reduce the viscosity of the SLES premix, and to the contrary, it may increase the viscosity. Additionally, the addition of a small amount of a mono-alcohol (e.g., ethanol) alone to an SLES premix reduces the viscosity of SLES only to some extent. However, when a hybrid of a mono-alcohol and a polyol is added to SLES, the viscosity of SLES is reduced significantly, much greater than the sum of the viscosity reductions caused by the mono-alcohol alone and by polyol alone.

The synergistic effect allows the use of less mono-alcohol in the SLES composition to reduce viscosity of the SLES composition to a desired level. Suitable mono-alcohols may include those having a low flash point, easily flammable, and low molecular weight alcohol. Thus, the use of less mono-alcohol improves the safety profile of the SLES composition.

According to some embodiments, the mono-alcohol is present in an amount ranging from about 1% to about 3%, from about 3% to about 6%, from about 6% to about 9%, from about 9% to about 12%, or from about 12% to about 15%, by weight of the SLES composition. According to some embodiments, the mono-alcohol amount is not more than 12%, more preferably, not more than 6%, by weight of the SLES composition.

According to one embodiment, the mono-alcohol may be selected from a group consisting of ethanol, isopropyl, propanol, butanol, pentanol, hexanol, heptanol, and octanol, and a mixture thereof. Preferably, the mono-alcohol is ethanol.

According to another embodiment, the polyol is selected from a group consisting of polyethylene glycol (PEG), glycerine, propylene glycol (PPG), glycol ethers, 2-methyl 1,3-propanediol, 1,3-propanediol, 1,5-pentanediol, glycerin, hexylene glycol, and mixtures thereof. Preferably, the polyol is PEG, glycerine, and propylene glycol. More preferably, the polyol is a low Mw polyethylene glycol. Most preferably, the polyol is PEG 100, PEG 200, PEG 300, PEG 400, PEG 500, PEG 600, or a combination thereof; the most preferred one is PEG 400. As conventionally known, the number 400 indicates the average molecular weight of Mw.

According to a further embodiment, the SLES composition does not include any additional component or solvent other than SLES, water, the mono-alcohol, and the polyol. According to yet another embodiment, the SLES composition may further include one or more components selected from alcohol ethoxylate, and sodium sulfite.

According to one embodiment, the polyol and the mono-alcohol have a weight ratio ranging from about 1:5 to about 5:1, preferably, from about 2:1 to about 3:1; and more preferably, about 3:1.

According to another embodiment, an SLES premix and the polyol have a weight ratio ranging from about 20:1 to about 1:1; preferably, from about 10:2 to about 10:3; and more preferably, about 10:3.

According to a further embodiment, an SLES premix and the mono-alcohol have a weight ratio ranging from about 60:1 to about 1:1; preferably from about 10:1 to about 10:2; and more preferably, about 10:1.

According to yet another embodiment, the weight of an SLES premix and a combined weight of the mono-alcohol and the polyol have a ratio ranging from about 15:1 to about 1:1; preferably, from about 10:4 to about 10:3; and more preferably, about 10:4.

In another aspect, the present invention provides a process for preparing a polyethoxylated alcohol sulfate composition with an improved rheology. The process comprises the step of blending a polyethoxylated alcohol sulfate with water, a mono-alcohol and a polyol, wherein the polyethoxylated alcohol sulfate having Formula (I) and is in an amount ranging from about 20% to about 80%, from about 25% to about 75%, from about 30% to about 70%, from about 35% to about 65%, from about 40% to about 60%, from about 45% to about 55%, from about 40% to about 45%, or about 42%, by the total weight of the polyethoxylated alcohol sulfate composition. In some embodiments, the polyethoxylated alcohol sulfate composition consists essentially of polyethoxylated alcohol sulfate composition, water, the mono-alcohol, and the polyol. In preferred embodiments, the polyethoxylated alcohol sulfate is SLES, and the resulting composition prepared by the above process can thus be called SLES composition or SLES blend.

In some embodiments, water is in an amount ranging from about 5% to about 35%, from about 10% to about 30%, from about 15% to about 25%, from about 17% to about 22%, about 18%, about 19%, about 20%, or about 21%, by weight of the polyethoxylated alcohol sulfate composition.

According to some embodiments of the SLES composition, SLES may be provided as a premix of neat SLES and water, which can be called SLES premix. A preferred SLES premix consists of SLES and water in a ratio of 7:3.

According to one embodiment, the SLES composition does not include any additional component or solvent other than SLES, water, a mono-alcohol, and a polyol. However, according to another embodiment, the SLES composition may further include one or more components selected from alcohol ethoxylate, and sodium sulfite.

According to one embodiment, the mono-alcohol may be selected from a group consisting of ethanol, isopropyl, propanol, butanol, pentanol, hexanol, heptanol, and octanol, and a mixture thereof. Preferably, the mono-alcohol is ethanol.

According to some embodiments, the mono-alcohol is present in an amount ranging from about 1% to about 3%, from about 3% to about 6%, from about 6% to about 9%, from about 9% to about 12%, or from about 12% to about 15%, by weight of the SLES composition. The mono-alcohol amount is not more than 12%, more preferably, not more than 6%, by weight of the SLES composition.

According to another embodiment, the polyol is selected from a group consisting of polyethylene glycol (PEG), glycerine, propylene glycol (PPG), glycol ethers, 2-methyl 1,3-propanediol, 1,3-propanediol, 1,5-pentanediol, glycerin, hexylene glycol, and mixtures thereof. Preferably, the polyol is PEG, glycerine, and propylene glycol. More preferably, the polyol is a low Mw polyethylene glycol, such as PEG 400.

According to one embodiment, the polyol and the mono-alcohol have a weight ratio ranging from about 1:5 to about 5:1, preferably, from about 2:1 to about 3:1; and more preferably, of about 3:1.

According to another embodiment, an SLES premix and the polyol have a weight ratio ranging from about 20:1 to about 1:1; preferably, from about 10:2 to about 10:3; and more preferably, of about 10:3.

According to a further embodiment, an SLES premix and the mono-alcohol have a weight ratio ranging from about 60:1 to about 1:1; preferably from about 10:1 to about 10:2; and more preferably, of about 10:1.

According to yet another embodiment, the weight of an SLES premix and a combined weight of the mono-alcohol and the polyol have a ratio ranging from about 15:1 to about 1:1; preferably, from about 10:4 to about 10:3; and more preferably, of about 10:4.

In some embodiments, an SLES premix is blended with the mono-alcohol first before blended with the polyol. In other embodiments, the mono-alcohol and the polyol are mixed first, which allows the preparation of a stock of the alcohol hybrid if needed, before further mixed the alcohol hybrid with the SLES premix.

In a further aspect, the present invention provides a detergent product by incorporating the polyethoxylated alcohol sulfate composition with an improved rheology, as described previously.

The detergent composition comprises:
(a) at least one nonionic surfactant, such as an alcohol ethoxylate, in an amount of about 10% to about 30%, about 15% to about 25%, or about 20% to about 25%, by weight of the detergent composition;
(b) a polyethoxylated alcohol sulfate blend, such as an SLES blend, and optionally another anionic surfactant, in an amount of about 8% to about 28%, about 12% to about 25%, about 15% to about 22%, or about 18% to about 22%, by weight of the detergent composition; wherein the polyethoxylated alcohol sulfate blend consists essentially of a polyethoxylated alcohol sulfate, a mono-alcohol, water, and a polyol.

(c) water in an amount of about 8% to about 20%, about 12% to about 25%, about 15% to about 22%, or about 18% to about 22%, by weight of the detergent composition.

In some embodiments, the types of SLES, water, mono-alcohol, and polyol suitable for use in the SLES blend and the relative weight ratios thereof, are the same as the SLES blend, which have been described previously. Thus, detailed information will not be repeated.

One advantage of the present invention is that because a polyol has been introduced by the SLES blend, no polyol may be needed to be separately added during the preparation to the detergent composition, unless the detergent composition is desirably in need of another polyol, or in an amount more than what have been provided via the SLES blend.

In other embodiments, the detergent composition further comprises an enzyme, a fatty acid, a fragrance composition, a color care agent, a polymer dispersant agent, an antidisposition agent, a softening agent, or a combination thereof.

The detergent composition may be provided as a liquid stored in a plastic bottle. It may also be enclosed in pouches made from a water-soluble polymer film to provide a unit dose form detergent product.

BRIEF DESCRIPTION OF THE DRAWINGS

FIG. 1. is a graph showing the rheology profiles of various SLES blends, as measured across a shear rate from 0.41 to 10 l/s.

DETAILED DESCRIPTION OF THE INVENTION

As used herein, "a," "an," or "the" means one or more unless otherwise specified.

The term "or" can be conjunctive or disjunctive.

The terms "container", "pouch", "pack", "pac", "unit dose", and "single dose" can be used interchangeably and can have one or two or multi-compartment (i.e., multi-chamber).

The terms "blend(s)" and "composition(s)" are used interchangeably.

The terms "solvent," "solvents," and "solvent system," mean a liquid or liquids used to dissolve or solvate other chemicals. In some cases, materials can also be dispersed within the solvent (i.e., Titanium Dioxide in water). In other cases, a solvent (i.e., solvent A) can initially exist as a solid and then be dissolved within solvent B, so solvent A can then act as a solvent itself (i.e., PEG 3350 in water). As used herein, the terms "solvent," "solvents," and "solvent system," do not include neutralization agents, such as, e.g., triethanolamine, monoethanolamine, and sodium hydroxide.

The term in a singular or plural form can mean both singular and plural forms. For example, "textile" or "textiles" may mean both textiles and textile; and "encapsulate" or "encapsulates" may mean both encapsulate and encapsulates.

The term "about" includes the recited number ±10%. For example, "about 10" means 9 to 11.

The phrase "substantially free of" means that a composition contains little no specified ingredient/component, such as less than about 1 wt %, 0.5 wt %, or 0.1 wt %, or below the detectable level of the specified ingredient. For example, the phrase "substantially free of a sulphate surfactant" refers to a liquid composition of the present invention that contains little or no sulphate surfactant.

As used herein, the "%" described in the present invention refers to the weight percentage unless otherwise indicated.

Unless stated otherwise, molecular weight of a polymer refers to weight average molecular weight.

The word "mono-alcohol" refers to a compound having only one hydroxyl group and having no other functional groups.

The word "polyol" refers to a compound having two or more hydroxyl groups and having no other functional groups.

The invention will now be described in details using SLES as an example. However, a person of ordinary skill in the art would understand that, in addition to reduce viscosity of SLES, the present invention is applicable to reduce viscosity of other polyethoxylated alcohol sulfates having the formula, R'—O—(C2H4O)n-SO3M', wherein R' is a C8-C20 alkyl group, n is from 1 to 20, and M' is a salt-forming cation, preferably, R' is C10-C18 alkyl, n is from 1 to 15, and M' is sodium, potassium, ammonium, alkylammonium, or alkanolammonium.

SLES Compositions with an Improved Rheology

In one aspect, the present invention provides an SLES composition with an improved rheology profile which allows the SLES composition to be flowable and processable, suitable for manufacturing processes.

The SLES composition in accordance with the present invention consists essentially of SLES, water, a mono-alcohol, and a polyol. SLES may be present in an amount ranging from about 20% to about 80%, from about 25% to about 75%, from about 30% to about 70%, from about 35% to about 65%, from about 40% to about 60%, from about 45% to about 55%, from about 40% to about 45%, or about 42%, by weight of the SLES composition.

In some embodiments, water is in an amount ranging from about 5% to about 35%, from about 10% to about 30%, from about 15% to about 25%, from about 17% to about 22%, about 18%, about 19%, about 20%, or about 21%, by weight of the polyethoxylated alcohol sulfate composition.

According to some embodiments of SLES compositions, SLES may be provided as a premix of neat SLES and water. A preferred SLES premix consists of SLES and water in a ratio of 7:3.

Mono-alcohols suitable for the present invention include those that have C1 to C6 mono-hydroxyl group and are in liquid or gel, preferably liquid form at room temperature. Preferably, the mono-alcohol does not create environmental and/or health hazards. In some embodiments, the mono-alcohol may be selected from a group consisting of ethanol, isopropyl, propanol, butanol, pentanol, hexanol, heptanol, and octanol, and a mixture thereof. Preferably, the mono-alcohol is selected from a group consisting of ethanol, isopropyl, propanol, butanol, and a mixture thereof. More preferably, the mono-alcohol is ethanol.

Polyols suitable for the present invention include those that have two or more hydroxyl groups and are in liquid or gel, preferably liquid form at room temperature. In some embodiments, the polyol is selected from a group consisting of polyethylene glycol (PEG), glycerine, propylene glycol (PPG), glycol ethers, 2-methyl 1,3-propanediol, 1,3-propanediol, 1,5-pentanediol, glycerin, hexylene glycol, and mixtures thereof. Preferably, the polyol is PEG, glycerine, and propylene glycol. More preferably, the polyol is a low Mw polyethylene glycol, such as PEG 400.

The inventors have unexpectedly noticed that, upon adding a polyol to the SLES/mono-alcohol blend, the viscosity level of SLES has been significantly reduced. It is known that a small molecule alcohol with a low boiling point (e.g., ethanol) may be used as a diluent, optionally with other solvents (e.g., water), to modify the rheology profile of SLES. For example, commercial SLES is supplied as a blend of SLES (60% wt), ethanol (12% wt), water (22% wt), alcohol ethoxylate 3EO (5% wt), and sodium sulfite (1% wt), in order to provide a flowable and processable form of SLES. The more ethanol added to SLES, the lower of the viscosity level of the resulting SLES composition.

It is known that a polyol may serve as a solvent for detergent products in general. But it is not known that a polyol could be used for viscosity adjustment for SLES. In fact, adding a polyol alone to SLES undesirably increase the viscosity of SLES. It is further unknown that a polyol and a mono-alcohol, when both are added to SLES, would cause a synergistic effect on the reduction of viscosity of SLES, meaning that the resulting viscosity reduction is much greater than the sum of the viscosity reductions caused by the addition of a mono-alcohol alone to SLES and by the addition of a polyol alone to SLES.

The present invention advantageously allows the use of less low flashing point mono-alcohol in the SLES composition while still providing SLES in a form with a desirable viscosity level. Without wishing to be bound by theory, it is believe that the addition of a polyol to an SLES/mono-alcohol blend synergistically enlarges the viscosity reduction effect caused by a small amount of alcohol, leading to an overall greater viscosity reduction.

According to some embodiments, the mono-alcohol is present in an amount ranging from about 1% to about 3%, from about 3% to about 6%, from about 6% to about 9%, from about 9% to about 12%, or from about 12% to about 15%, by weight of the SLES composition. In some embodiments, the mono-alcohol amount is less than 12%, more preferably, less than 6%, by weight of the SLES composition.

According to some embodiments, the polyol and the mono-alcohol have a weight ratio ranging from about 1:5 to about 5:1, from about 1:4 to about 4:1, from about 1:3 to about 3:1, or from about 1:2 to about 2:1. According to other embodiments, the polyol and the mono-alcohol have a weight ratio ranging from about 1:5 to about 1:4, from about 1:4 to about 1:3, from about 1:3 to about 1:2, from about 1:2 to about 1:1, from about 1:1 to about 1:2, from about 2:1 to about 3:1, from about 3:1 to about 4:1, or from about 4:1 to about 5:1. According to further embodiments, the polyol and the mono-alcohol have a weight ratio of about 1:5, about 1:4, about 1:3, about 1:2, about 1:1, about 2:1, about 3:1, about 4:1, or about 5:1; preferably, about 2:1, about 3:1.

According to some embodiments, an SLES premix and the polyol have a weight ratio ranging from about 20:1 to about 1:1, from about 15:1 to about 2:1, from about 10:1 to about 3:1, about 5:1 to about 4:1, about 5:4, about 5:3, or about 5:2; preferably, about 5:3. According to other embodiments, an SLES premix and the polyol have a weight ratio ranging from about 10:1 to about 10:5, from about 10:2 to about 10:4, about 10:1, or about 10:3; preferably from about 10:2 to about 10:3; and more preferably, about 10:3.

According to some embodiments, an SLES premix and the mono-alcohol have a weight ratio ranging from about 60:1 to about 1:1, from about 50:1 to about 2:1, from about 40:1 to about 3:1, about 30:1 to about 4:1, about 20:1 to about 5:1, from about 15:1 to about 5:1, about 10:1 to about 5:1, about 15:1, about 12.5:1, about 10:1, about 7.5:1, about 5:1; preferably from about 10:1 to about 10:2; and more preferably, about 10:1.

According to further embodiments, the weight of an SLES premix and a combined weight of the mono-alcohol and the polyol have a ratio ranging from about 15:1 to about 1:1, from about 14:1 to about 2:1, from about 13:1 to about 3:1, about 12:1 to about 4:1, from about 11:1 to about 5:1, from about 10:1 to about 6:1, about 9:1 to about 7:1. According to yet further embodiments, the weight of an SLES premix and a combined weight of the mono-alcohol and the polyol have a ratio of about 10:5, about 10:4, about 10:3, about 10:2, about 10:1; and more preferably, about 10:4.

According to a further embodiment, the SLES composition does not include any additional component or solvent other than SLES, water, the mono-alcohol, and the polyol. According to yet another embodiment, the SLES composition further includes one or more components selected from a group consisting of alcohol ethoxylate, and sodium sulfite.

Process for Preparing SLES Blends

In accordance with the present invention, a process for preparing an SLES composition with an improved rheology comprising: blending SLES with water, a mono-alcohol, and a polyol.

SLES is present in an amount ranging from about 20% to about 80%, from about 25% to about 75%, from about 30% to about 70%, from about 35% to about 65%, from about 40% to about 60%, from about 45% to about 55%, from about 40% to about 45%, or about 42%, by the total weight of the SLES composition.

In some embodiments, water is in an amount ranging from about 5% to about 35%, from about 10% to about 30%, from about 15% to about 25%, from about 17% to about 22%, about 18%, about 19%, about 20%, or about 21%, by weight of the SLES composition.

According to some embodiments of SLES compositions, SLES may be provided as a premix of neat SLES and water. A preferred SLES premix consists of SLES and water in a ratio of 7:3.

In some embodiments, the SLES composition does not include any additional component or solvent other SLES, water, a mono-alcohol, and a polyol. In other embodiments, the SLES composition may include one or more components selected from a group consisting of alcohol ethoxylate, and sodium sulfite.

The types and the amounts of the mono-alcohol and the polyol, including preferred embodiments and the relative weight ratios among the mono-alcohol, the polyol, and the SLES premix, that are suitable for the process are substantially the same as those described in the section, SLES Compositions With An Improved Rheology. Thus, details of the formulation will not be repeated.

In some embodiments, the SLES premix is blended with the mono-alcohol first before blended with the polyol. In other embodiments, the polyol and the mono-alcohol are mixed first to prepare a stock solution before such stock solution is then mixed with the SLES premix. In further embodiments, all of the components are added and mixed altogether.

The mixing step can be conducted by any conventional equipment, following conventional methods. The components may be heated to facilitate the mixing, followed by cooling. Preferably, all the components are mixed until they become homogenous.

Detergent Compositions

A further aspect of the present invention provides a detergent composition which comprises the SLES blend described herein.

In one embodiment, the detergent composition comprises:

(a) at least one nonionic surfactant, such as an alcohol ethoxylate, in an amount of about 10% to about 30%, about 15% to about 25%, or about 20% to about 25%, by weight of the detergent composition;

(b) an SLES blend, and optionally another anionic surfactant, in an amount of about 8% to about 28%, about 12% to about 25%, about 15% to about 22%, or about 18% to about 22%, by weight of the detergent composition; wherein the SLES blend consists essentially of SELS, a mono-alcohol, water, and a polyol;

(c) water in an amount of about 8% to about 20%, about 12% to about 25%, about 15% to about 22%, or about 18% to about 22%, by weight of the detergent composition.

Nonionic Surfactants

Examples of nonionic surfactants suitable for the present invention include, but are not limited to, polyalkoxylated alkanolamides, polyoxyalkylene alkyl ethers, polyoxyalkylene alkylphenyl ethers, polyoxyalkylene sorbitan fatty acid esters, polyoxyalkylene sorbitol fatty acid esters, polyoxyethylene polyoxypropylene alkyl ethers, polyoxyalkylene castor oils, polyoxyalkylene alkylamines, glycerol fatty acid esters, alkylglucosamides, alkylglucosides, alkylamine oxides, amine oxide surfactants, alkoxylated fatty alcohols, or a mixture thereof. In some embodiments, the nonionic surfactant is alcohol ethoxylate (AE), alcohol propoxylate, or a mixture thereof. In other embodiments, the nonionic surfactant is AE.

The AE may be primary and secondary alcohol ethoxylates, especially the $C_8$-$C_{20}$ aliphatic alcohols ethoxylated with an average of from 1 to 20 moles of ethylene oxide per mole of alcohol, and more especially the $C_{10}$-$C_{15}$ primary and secondary aliphatic alcohols ethoxylated with an average of from 1 to 10 moles, or from 3 to 8 moles of ethylene oxide per mole of alcohol.

Exemplary AEs are the condensation products of aliphatic $C_8$-$C_{20}$, preferably $C_8$-$C_{16}$, primary or secondary, linear or branched chain alcohols with ethylene oxide. In some embodiments, the alcohol ethoxylates contain 1 to 20, or 3 to 8 ethylene oxide groups, and may optionally be end-capped by a hydroxylated alkyl group.

In one embodiment, the AE has Formula (II):

$$R_2-(-O-C_2H_4-)_m-OH \qquad (II)$$

wherein $R_2$ is a hydrocarbyl group having 8 to 16 carbon atoms, 8 to 14 carbon atoms, 8 to 12 carbon atoms, or 8 to 10 carbon atoms; and m is from 1 to 20, or 3 to 8.

The hydrocarbyl group may be linear or branched, and saturated or unsaturated. In some embodiments, $R_2$ is a linear or branched $C_8$-$C_{16}$ alkyl or a linear group or branched $C_8$-$C_{16}$ alkenyl group. Preferably, $R_2$ is a linear or branched $C_8$-$C_{16}$ alkyl, $C_8$-$C_{14}$ alkyl, or $C_8$-$C_{10}$ alkyl group. In case (e.g., commercially available materials) where materials contain a range of carbon chain lengths, these carbon numbers represent an average. The alcohol may be derived from natural or synthetic feedstock. In one embodiment, the alcohol feedstock is coconut, containing predominantly $C_{12}$-$C_{14}$ alcohol, and oxo $C_{12}$-$C_{15}$ alcohols.

One suitable AE is Tomadol® 25-7 (available from Air Product). Other suitable AEs include Genapol® C200 (available from Clariant), which is a coco alcohol having an average degree of ethoxylation of 20.

Anionic Surfactants

In some embodiments, the anionic surfactant is a polyethoxylated alcohol sulfate, such as those sold under the trade name CALFOAM® 303 (Pilot Chemical Company, California). Such materials, also known as alkyl ether sulfates (AES) or alkyl polyethoxylate sulfates of Formula (I), such as SLES, as described before.

In other embodiments, the anionic surfactant may be linear alkylbenzene sulfonic acid (LAS) or a salt thereof, alkyl ethoxylated sulphate, alkyl propoxy sulphate, alkyl sulphate, or a mixture thereof. Linear alkylbenzenesulfonate (LAS) is a water-soluble salt of a linear alkyl benzene sulfonate having between 8 and 22 carbon atoms of the linear alkyl group. The salt can be an alkali metal salt, or an ammonium, alkylammonium, or alkanolammonium salt. In one embodiment, the LAS comprises an alkali metal salt of $C_{10}$-$C_{16}$ alkyl benzene sulfonic acids, such as $C_{11}$-$C_{14}$ alkyl benzene sulfonic acids.

However, in further embodiments, the detergent compositions are substantially free of LAS.

SLES Blend

As described herein, the SLES blend consists essentially of SLES, water, a mono-alcohol, and a polyol. The types and the amounts of the components of the SLES blend and the relative weight ratios thereof, are the same as what have described in the section, SLES Compositions With An Improved Rheology. Thus, details of the formulation will not be repeated.

Optionally, Other Ingredients in the Detergent Compositions

In some embodiments, the detergent composition may comprise a cationic surfactant, an ampholytic surfactant, a zwitterionic surfactant, or mixtures thereof.

In other embodiments, the detergent composition may comprise a fatty acid. Suitable fatty acid may be any fatty acid having formula: $R_3-C(O)OH$, wherein $R_3$ is a $C_5$-$C_{21}$ linear or branched aliphatic group. Preferably, the $R_3$ is a $C_{13}$-$C_{21}$ linear or branched aliphatic group. In a preferred embodiment, the fatty acid is dodecanoic acid (also known as coconut fatty acid).

In further embodiments, the detergent composition may comprise a fragrance composition, a color care agent, a soil releasing polymer, an anti-disposition agent, a softening agent, or a combination thereof. It may also comprise a whitening agent, a brightening agent, a color/texture rejuvenating agent, a bleaching catalyst, a bleaching agent, a bleach activator, a buffer, a surfactant stabilizer, a neutralization agent, a builder, an enzyme, a dye (colorant), a dispersing agent, a defoamer, an anticorrosion agent, a deodorizing agent, a preservative, a bittering agent, and/or a biocidal agent.

Unit Dose

The detergent composition may be filled in plastic bottles to provide bottled products. It may also be enclosed in pouches to provide unit dose detergent pacs, where the pouches are formed from a water-soluble or water-dispersible film material, which fully encloses the detergent composition. The detergent composition may be in the form of a solution or a suspension, although a solution is preferred. In some embodiments, the container comprises at least two compartments, with one compartment receiving the liquid composition and other compartment(s) receiving additional compositions. Each compartment may have the same or different compositions. The additional compositions may be liquid, solid, gel, or mixtures thereof.

The water-soluble or water-dispersible film material may be selected from the group consisting of polyvinyl alcohol (PVOH), polyvinyl acetate (PVA), film forming cellulosic polymer, polyacrylic acid, polyacrylamide, polyanhydride, polysaccharide, polyvinyl pyrrolidone, polyalkylene oxide, cellulose, cellulose ether, cellulose ester, cellulose amide, polyvinyl acetate, polycarboxylic acid and salt, polyaminoacid, polyamide, natural gums, polyacrylate, water-soluble acrylate copolymer, methylcellulose, carboxymethylcellulose sodium, dextrin, ethylcellulose, hydroxyethyl cellulose, maltodextrin, polymethacrylate, polyvinyl alcohol copolymer, and hydroxypropyl methyl cellulose (HPMC), and a mixture thereof. In preferred embodiments, the water-soluble or water-dispersible film material is selected from polyvinyl alcohol or polyvinyl acetate.

As stated earlier, the present invention is not limited to SLES, the present invention is applicable to the reduction of viscosity of other polyethoxylated alcohol sulfates, i.e., alkyl ether sulfates (AES) or alkyl polyethoxylate sulfates, having the following formula (I):

R'—O—(C2H4O)n-SO3M'   (I)

wherein R' is a C8-C20 alkyl group, n is from 1 to 20, and M' is a salt-forming cation, preferably, R' is C10-C18 alkyl, n is from 1 to 15, and M' is sodium, potassium, ammonium, alkylammonium, or alkanolammonium.

Accordingly, as also described in the Brief Summary of the Invention, the present invention also provides (1) a polyethoxylated alcohol sulfate blend consisting essentially of polyethoxylated alcohol sulfate, water, a mono-alcohol, and a polyol; (2) a method for preparing the polyethoxylated alcohol sulfate blend; and (3) a detergent composition or a unit dose detergent product comprising at least one nonionic surfactant, the polyethoxylated alcohol sulfate blend and a solvent system.

The types and the amounts of the components suitable for use in the invention covering a polyethoxylated alcohol sulfates are substantially the same as those used in the embodiments, wherein the anionic surfactant is SLES. Thus, details of the information will not be repeated. A person of ordinary skill in the art would understand the scope of the present invention covers all the embodiments, wherein SLES is simply substituted with a polyethoxylated alcohol sulfate of Formula (I). Details of the embodiments having a polyethoxylated alcohol sulfate blend with an improved rheology will not be elaborated herein because it would be substantially a repeat.

EXAMPLES

The following examples are intended to further illustrate the invention and are not intended to limit the invention in any way.

Example 1

Preparation of SLES Compositions

In order to compare differences in rheology of SLES as a result of the addition of ethanol and/or at least one of other alcohols, SLES compositions of eight formulas were prepared: Formula 1 includes 70 parts SLES and 30 parts water only; Formula 2 includes 60 parts a mixture of SLES and water (SLES:water=7:3), 12 parts ethanol, and no a polyol; Formula 3 includes 60 parts SLES and water mixture (SLES:water=7:3), 6 parts ethanol, and no polyol; Formula 4 includes 60 parts SLES and water mixture (SLES:water=7:3), no ethanol, and 12 parts PEG 400; Formula 5 includes 60 parts SLES and water mixture (SLES:water=7:3), 6 parts ethanol, and 12 parts PEG 400; Formula 6 includes 60 parts SLES and water mixture (SLES:water=7:3), 6 parts ethanol, and 12 parts propylene glycol (PG); Formula 7 includes 60 parts SLES and water mixture (SLES:H2O=7:3), 6 parts ethanol, and 12 parts glycerine (Gly); and Formula 8 includes 60 parts SLES and water mixture (SLES:water=7:3), 6 parts ethanol, and 18 parts PEG 400. The compositions were prepared at a laboratory scale of 60 g of each final SLES composition.

SLES composition of Formula 1 was prepared by mixing neat SLES and water. SLES compositions of Formulas 2 to 8 were prepared generally as follows: 1) providing a mixing container with an overhead stirrer; 2) adding water (if applicable) to the container; 3) adding SLES:water (7:3), ethanol (if applicable) and PG/Gly/PEG 400 (if applicable), and optionally other ingredients, in the container and mixing all of the ingredients with the stirrer until a homogenous mixture is obtained. During the process, each composition was checked for clumps which were broken as required. The mixing process can be conducted at an elevated temperature to facilitate the mixing by heating the components in the container directly or indirectly (i.e., heating up the container). Finally, the SLES compositions were cooled to room temperature.

Example 2

Rheology Measurement of the SLES Compositions

Rheology measurements were conducted using an AR2000-EX Rheometer with a test method of increasing the shear rate from 0.41 to 10 l/s over 5 minutes at 20° C. with a geometry cone of 40 mm, 1:59:49 (degree:min:sec), and a truncation gap of 52 microns (cone is part number 511406.901). Viscosities (Pa·S) of the SLES Blend Formulations prepared in Example 1 were measured and reported in Table 1. "SLES*" in the Table of the application stands for a mixture of SLES and water with a ratio of 7:3.

TABLE 1

| | Formula | | | | | | | |
|---|---|---|---|---|---|---|---|---|
| | 1 | 2 | 3 | 4 | 5 | 6 | 7 | 8 |
| Shear Rate (1/s) | SLES* only, no alcohol(s) | SLES*:Ethanol:(PG/Gly/PEG) = 60:12:0 | SLES*:Ethanol:(PG/Gly/PEG) = 60:6:0 | SLES*:Ethanol:PEG 400 = 60:0:12 | SLES*:Ethanol:PEG 400 = 60:6:12 | SLES*:Ethanol:PG = 60:6:12 | SLES*:Ethanol:Gly = 60:6:12 | SLES*:Ethanol:PEG 400 = 60:6:18 |
| | | | | Viscosity (Pa · S) | | | | |
| 0.41 | 95.510 | 0.429 | 55.070 | 121.800 | 1.511 | 4.487 | 25.100 | 1.086 |
| 0.75 | 49.480 | 0.294 | 28.730 | 71.860 | 0.916 | 2.059 | 11.140 | 0.646 |
| 1.08 | 32.980 | 0.232 | 18.620 | 53.320 | 0.696 | 1.209 | 7.257 | 0.482 |
| 1.41 | 24.730 | 0.221 | 13.910 | 44.090 | 0.565 | 0.841 | 5.646 | 0.425 |
| 1.73 | 19.840 | 0.196 | 11.310 | 38.570 | 0.507 | 0.662 | 4.674 | 0.368 |
| 2.06 | 16.660 | 0.176 | 9.707 | 34.820 | 0.449 | 0.602 | 4.111 | 0.337 |

TABLE 1-continued

| | Formula | | | | | | | |
|---|---|---|---|---|---|---|---|---|
| | 1 | 2 | 3 | 4 | 5 | 6 | 7 | 8 |
| Shear Rate (1/s) | SLES* only, no alcohol(s) | SLES*:Ethanol:(PG/Gly/PEG) = 60:12:0 | SLES*:Ethanol:(PG/Gly/PEG) = 60:6:0 | SLES*:Ethanol:PEG 400 = 60:0:12 | SLES*:Ethanol:PEG 400 = 60:6:12 | SLES*:Ethanol:PG = 60:6:12 | SLES*:Ethanol:Gly = 60:6:12 | SLES*:Ethanol:PEG 400 = 60:6:18 |
| | | | | Viscosity (Pa · S) | | | | |
| 2.39 | 14.550 | 0.176 | 8.653 | 32.240 | 0.440 | 0.494 | 3.790 | 0.318 |
| 2.72 | 12.920 | 0.190 | 7.903 | 30.070 | 0.431 | 0.433 | 3.528 | 0.316 |
| 3.06 | 11.770 | 0.201 | 7.339 | 28.350 | 0.419 | 0.409 | 3.319 | 0.316 |
| 3.39 | 10.640 | 0.195 | 6.842 | 26.940 | 0.422 | 0.387 | 3.061 | 0.324 |
| 3.71 | 9.708 | 0.194 | 6.469 | 25.590 | 0.441 | 0.390 | 2.950 | 0.329 |
| 4.05 | 9.031 | 0.208 | 6.157 | 24.550 | 0.430 | 0.398 | 2.828 | 0.319 |
| 4.37 | 8.616 | 0.220 | 5.860 | 23.710 | 0.420 | 0.402 | 2.740 | 0.313 |
| 4.71 | 8.195 | 0.246 | 5.591 | 22.630 | 0.411 | 0.347 | 2.651 | 0.306 |
| 5.03 | 7.684 | 0.253 | 5.284 | 21.620 | 0.419 | 0.307 | 2.593 | 0.303 |
| 5.37 | 7.263 | 0.250 | 5.039 | 20.760 | 0.416 | 0.311 | 2.509 | 0.292 |
| 5.70 | 6.970 | 0.274 | 4.883 | 20.290 | 0.397 | 0.312 | 2.447 | 0.291 |
| 6.03 | 6.687 | 0.296 | 4.733 | 20.040 | 0.393 | 0.287 | 2.382 | 0.297 |
| 6.36 | 6.276 | 0.294 | 4.603 | 19.660 | 0.393 | 0.277 | 2.319 | 0.287 |
| 6.68 | 6.086 | 0.290 | 4.463 | 19.420 | 0.380 | 0.279 | 2.263 | 0.282 |
| 7.02 | 5.888 | 0.280 | 4.273 | 19.180 | 0.380 | 0.264 | 2.203 | 0.284 |
| 7.35 | 5.652 | 0.272 | 4.125 | 18.970 | 0.378 | 0.266 | 2.170 | 0.280 |
| 7.68 | 5.586 | 0.306 | 4.008 | 18.670 | 0.372 | 0.256 | 2.141 | 0.285 |
| 8.01 | 5.383 | 0.287 | 3.917 | 18.210 | 0.374 | 0.260 | 2.080 | 0.279 |
| 8.34 | 5.295 | 0.283 | 3.788 | 17.860 | 0.366 | 0.256 | 2.072 | 0.281 |
| 8.67 | 5.093 | 0.266 | 3.698 | 17.520 | 0.368 | 0.258 | 2.048 | 0.281 |
| 8.99 | 4.923 | 0.281 | 3.611 | 17.450 | 0.358 | 0.262 | 2.050 | 0.282 |
| 9.32 | 4.756 | 0.276 | 3.534 | 17.230 | 0.361 | 0.258 | 1.993 | 0.281 |
| 9.66 | 4.613 | 0.267 | 3.456 | 16.900 | 0.352 | 0.259 | 1.988 | 0.281 |
| 9.99 | 4.483 | 0.295 | 3.346 | 16.450 | 0.356 | 0.255 | 1.992 | 0.278 |

FIG. 1 is a graph showing the rheology changes of SLES as a result of the addition of an alcohol hybrid, based on the data of Table 1.

As shown in FIG. 1, the addition of ethanol reduced the viscosity of SLES, however, the extent of reduction depended on the ratio of SLES and ethanol in the composition. When the SLES premix and ethanol had a weight ratio of 60 parts to 12 parts (Formula 2), the viscosity of the SLES blend was reduced significantly, from 32,980 cP (the SLES premix, Formula 1) to 0.232 cP at a shear rate of 1.08 1/s. When the SLES premix and ethanol had a weight ratio of 60 parts to 6 parts (Formula 3), the viscosity was only reduced to 18,620 cP from 32,980 cP (the SLES premix, Formula 1) at a shear rate of 1.08 1/s.

FIG. 1 shows that the addition of a polyol, alone to the SLES premix did not reduce the viscosity of SLES. To the contrary, it may increase the viscosity. For example, the viscosity of the resulting SLES premix and PEG in a weight ratio of 60 parts to 12 parts was increased to 53,320 cP from 32,980 cP (the SLES premix, Formula 1) at a shear rate of 1.08 1/s.

However, when PEG 400 was added to an SLES blend having the SLES premix and ethanol, it greatly improved the rheology of the SLES blend.

When an additional 12 parts of PEG 400 was added to the SLES blend having the SLES premix and ethanol in a ratio of 60 parts:6 parts, the viscosity of the SLES blend (Formula 5) further dropped from 18,620 cP to 696 cP at a shear rate of 1.08 1/s. When an additional 18 parts of PEG 400 was added to the SLES blend having the SLES premix and ethanol in a ratio of 60 parts:6 parts, the viscosity of the SLES blend (Formula 8) further dropped from 18,620 cP to 482 cP at a shear rate of 1.08 1/s.

The use of propylene glycol or glycerine to substitute PEG 400 in a blend of SLES premix, ethanol, and PEG 400 also showed a decrease in viscosity of SLES, although the extent of decrease is not as much as when PEG was used. Nevertheless, the he SLES blends, i.e., premix SLES, ethanol, and PG/Gly/PEG 400, all supply SLES with a viscosity that is a manageable level from a process point of view.

The rheology of compositions of Formulas 5 and 8 showed a clear trend that the more PEG 400 added to the SLES blend, the lower viscosity of the SLES blend. Additionally, less ethanol is required to reduce viscosity of the SLES composition if PEG 400 is added.

FIG. 1 shows that there existed a synergic effect in lowering the viscosity level of SLES as a resulting of adding both ethanol and a polyol, such as PEG 400, propylene glycol, and glycerine. For example, when only PEG 400 (12 parts) is added to the SLES premix, the rheology of the resulting composition of Formula 4 became worse (more viscous) than that of the composition of Formula 1. When only ethanol (6 parts) is added to the SLES premix, the rheology of the resulting composition of Formula 3 only improved modestly. However, when both PEG 400 (12 parts) and ethanol (6 parts) were added to the SLES premix, the rheology of the resulting composition of Formula 5 showed a significant improvement compared to that of the composition of Formula 1.

Example 3

Preparation of Laundry Detergent Compositions Comprising SLES

Laundry detergent compositions using the SLES blend, as set forth in Table 2, were prepared by following conventional methods of preparation. Instead of using highly viscous SLES, a flowable and processable SLES blend was used during the manufacturing process.

| Description | Composition 1 (% wt) | Composition 2 (% wt) | Composition 3 (% wt) |
|---|---|---|---|
| C12-C15 Alcohol Ethoxylate 7EO | 23.1 | 23.1 | 23.1 |
| PEG 400 | 18.5 | 0 | 0 |
| SLES Blend (60 parts SLES premix, 12 parts ethanol) | 18.72 | 0 | 0 |
| SLES Blend (60 parts SLES premix, 6 parts ethanol, 12 parts PEG 400) | 0 | 20.26 | 0 |
| SLES Blend (60 parts SLES premix, 6 parts ethanol, 18 parts PEG 400) | 0 | 0 | 21.85 |
| Glycerine | 9 | 9 | 9 |
| Propylene Glycol | 7 | 7 | 7 |
| Bases | 1.5 | 1.5 | 1.5 |
| Fatty Acid | 4 | 4 | 4 |
| Enzymes | 1.5 | 1.5 | 1.5 |
| Other Ingredients | 1.1 | 1.1 | 1.1 |
| Water | 13.6 | 12 | 10.5 |
| Polymeric Dispersant | 2 | 2 | 2 |
| Total | 100 | 100 | 100 |

As shown in Compositions 2 and 3, one advantage of using the SLES blend having PEG 400 as a co-diluent is that, depending on the amount of PEG 400 needed in a detergent composition, no PEG may be needed to be separately added during the preparation to the detergent composition. Thus, the present invention creates a way to introduce PEG 400 into the detergent product without the need of a dedicated PEG 400 ingredient tank because PEG 400 is provided in the SLES blend.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A polyethoxylated alcohol sulfate blend consisting essentially of:
   a polyethoxylated alcohol sulfate having Formula (I):

$$R'—O—(C2H4O)_n-SO3M' \quad (I)$$

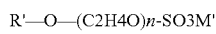

wherein R' is C10-C18 alkyl, n is from 1 to 15, and M' is sodium, potassium, ammonium, alkylammonium, or alkanolammonium,
   ethanol,
   a polyol chosen from the group consisting of polyethylene glycol, propylene glycol, glycerine, and combinations thereof, and
   water;
   wherein the polyethoxylated alcohol sulfate is present in an amount ranging from about 20% to about 80% by weight of the blend; and
   wherein the polyethoxylated alcohol sulfate, the ethanol, and the polyol are present in a weight ratio of actives of 7:1:2 to 7:1:3.

2. The polyethoxylated alcohol sulfate blend of claim 1, wherein the polyethoxylated alcohol sulfate is sodium laureth ether sulfate (SLES).

3. The polyethoxylated alcohol sulfate blend according to claim 1, wherein the polyol is PEG 400.

4. The polyethoxylated alcohol sulfate blend according to claim 1, consisting of the polyethoxylated alcohol sulfate, the water, the ethanol, and the polyol.

5. The polyethoxylated alcohol sulfate blend according to claim 1, having a viscosity of less than 100 Pa·S over a shear rate between 0.41 to 10 1/s at 20° C.

6. The polyethoxylated alcohol sulfate blend according to claim 1, having a viscosity of less than 26 Pa·S over a shear rate between 0.41 to 10 1/s at 20° C.

7. The polyethoxylated alcohol sulfate blend of claim 1, wherein the polyethoxylated alcohol sulfate is sodium laureth ether sulfate and the polyol is polyethylene glycol 400.

8. The polyethoxylated alcohol sulfate blend of claim 1, wherein the polyethoxylated alcohol sulfate is sodium laureth ether sulfate, the polyol is propylene glycol and the sodium laureth ether sulfate, the ethanol, and the propylene glycol are present in a weight ratio of actives of 7:1:2.

9. The polyethoxylated alcohol sulfate blend of claim 1, wherein the polyethoxylated alcohol sulfate is sodium laureth ether sulfate, the polyol is glycerine and the sodium laureth ether sulfate, the ethanol, and the glycerine are present in a weight ratio of actives of 7:1:2.

10. The polyethoxylated alcohol sulfate blend of claim 4, wherein the polyethoxylated alcohol sulfate is sodium laureth ether sulfate and the polyol is polyethylene glycol 400.

11. The polyethoxylated alcohol sulfate blend of claim 4, wherein the polyethoxylated alcohol sulfate is sodium laureth ether sulfate, the polyol is propylene glycol and the sodium laureth ether sulfate, the ethanol, and the propylene glycol are present in a weight ratio of actives of 7:1:2.

12. The polyethoxylated alcohol sulfate blend of claim 4, wherein the polyethoxylated alcohol sulfate is sodium laureth ether sulfate, the polyol is glycerine and the sodium laureth ether sulfate, the ethanol, and the glycerine are present in a weight ratio of actives of 7:1:2.

13. The polyethoxylated alcohol sulfate blend of claim 1, wherein the polyol is chosen from the group consisting of propylene glycol, glycerine, and combinations thereof.

* * * * *